United States Patent
Barham

(10) Patent No.: US 8,398,398 B1
(45) Date of Patent: Mar. 19, 2013

(54) FOAM PAD USED WITH TUBULAR MEMBER TO VACUUM FLUIDS FROM AN ORAL CAVITY

(76) Inventor: William L. Barham, Mt. Airy, NC (US)

(*) Notice: Subject to any disclaimer, the term of this patent is extended or adjusted under 35 U.S.C. 154(b) by 0 days.

(21) Appl. No.: 12/932,511

(22) Filed: Feb. 25, 2011

Related U.S. Application Data

(60) Provisional application No. 61/338,819, filed on Feb. 25, 2010.

(51) Int. Cl.
*A61C 17/06* (2006.01)
*A61C 17/14* (2006.01)

(52) U.S. Cl. .......................................................... 433/91

(58) Field of Classification Search .............. 433/91–96, 433/29–31, 136, 140; 604/902, 275, 276, 604/35, 36, 319, 171, 164.08, 263, 327, 328, 604/355; 600/573, 576; 15/403
See application file for complete search history.

(56) References Cited

U.S. PATENT DOCUMENTS

| | | | | |
|---|---|---|---|---|
| 2,955,311 A * | 10/1960 | Jurkanis | ........................ | 401/203 |
| 3,081,475 A * | 3/1963 | Vosbikian et al. | ........... | 15/244.1 |
| 3,324,855 A | 6/1967 | Heimlich | | |
| 3,428,987 A * | 2/1969 | Loston | ............................ | 15/114 |
| 3,983,596 A * | 10/1976 | Siemund | ...................... | 15/244.1 |
| 4,058,896 A | 11/1977 | Moore | | |
| 4,233,025 A * | 11/1980 | Larson et al. | .................. | 433/136 |
| 4,265,621 A | 5/1981 | McVey | | |
| 4,867,747 A | 9/1989 | Yarger | | |
| 5,076,787 A | 12/1991 | Overmyer | | |
| 5,078,603 A * | 1/1992 | Cohen | .............................. | 433/91 |
| 5,094,616 A | 3/1992 | Levenson | | |
| 5,151,094 A | 9/1992 | Hanifl | | |
| 5,407,353 A * | 4/1995 | Clementz | ......................... | 433/93 |
| 5,762,496 A | 6/1998 | Albertsson et al. | | |
| 5,842,488 A * | 12/1998 | Belleau et al. | ................. | 132/320 |
| 5,924,866 A * | 7/1999 | Eldreth | .......................... | 433/140 |
| 6,044,513 A * | 4/2000 | Penn | ................................ | 15/118 |
| 6,068,477 A | 5/2000 | Mahlmann | | |
| 6,159,226 A | 12/2000 | Kim | | |
| 6,183,254 B1 | 2/2001 | Cohen | | |
| 6,546,587 B2 * | 4/2003 | Christiansen | .................... | 15/231 |
| 7,238,023 B1 | 7/2007 | Enos | | |
| 7,335,023 B2 * | 2/2008 | Mahlmann | ........................ | 433/96 |
| 7,347,691 B1 * | 3/2008 | Kelly, Sr. | .......................... | 433/91 |
| 7,458,128 B2 * | 12/2008 | Smith et al. | ....................... | 15/247 |
| 2004/0014002 A1 | 1/2004 | Ludgren | | |
| 2006/0110702 A1 | 5/2006 | Mahlmann | | |
| 2008/0047087 A1 * | 2/2008 | Levy et al. | .................... | 15/210.1 |

* cited by examiner

*Primary Examiner* — Yogesh Patel
(74) *Attorney, Agent, or Firm* — Robert W. Pitts

(57) ABSTRACT

A dental suction apparatus 2 includes a tubular vacuum member 10, such as a tubular vacuum tip or aspirator, and a protective foam pad 20. The pad is mounted on a distal end 12 of the tubular vacuum member through a first opening 32 and partially through a second opening 34. In a folded operative position, the foam member 20 not only protects the patient's mouth, but creates a larger surface through which fluids and debris particles can be drawn though the influence of a vacuum.

8 Claims, 4 Drawing Sheets

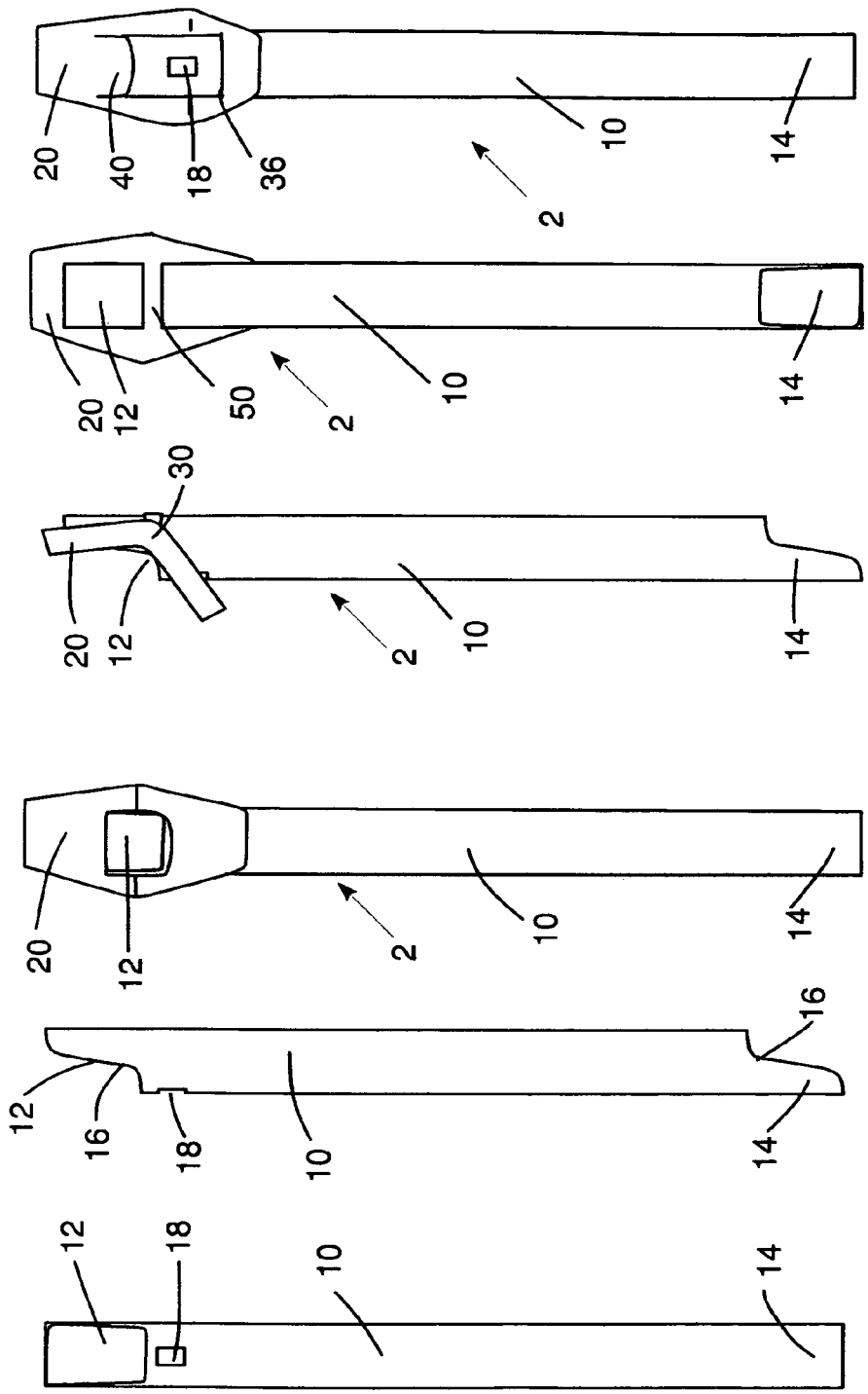

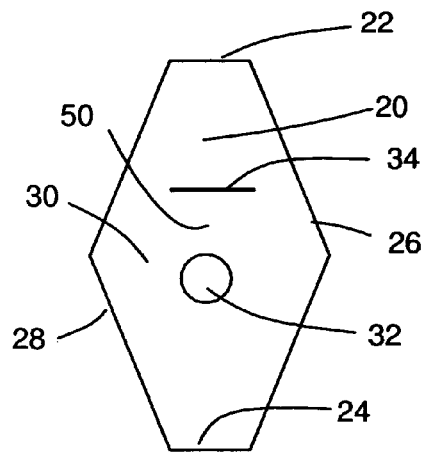
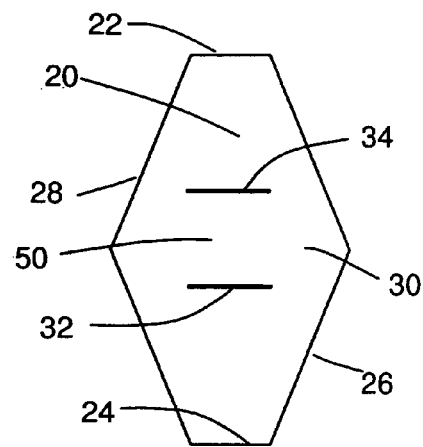
FIG 3A  FIG 3B
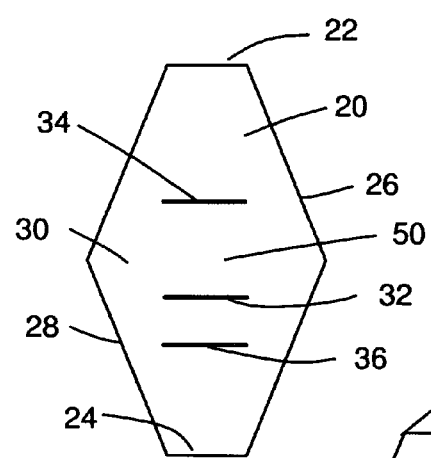
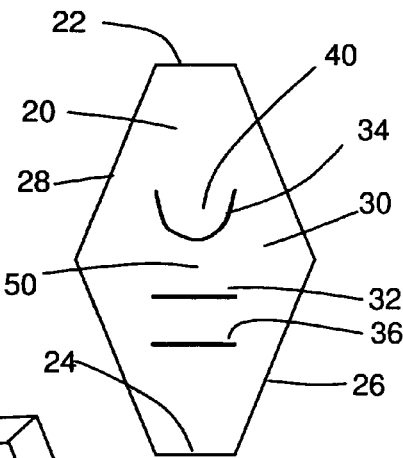
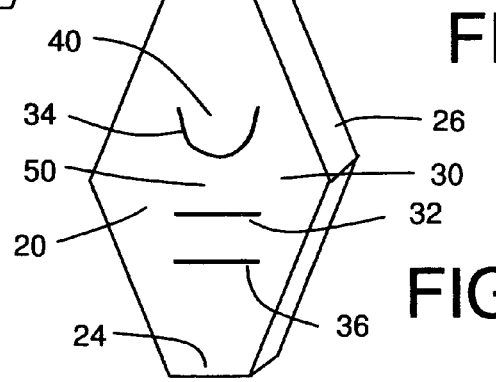
FIG 3C  FIG 3D  FIG 4

FOAM PAD USED WITH TUBULAR MEMBER TO VACUUM FLUIDS FROM AN ORAL CAVITY

CROSS REFERENCE TO PRIOR CO-PENDING APPLICATION

This application claims the benefit of prior filed, U.S. Provisional Patent Application 61/338,819 filed on Feb. 25, 2010.

BACKGROUND OF THE INVENTION

1. Field of the Invention

This invention is intended for use in removing fluids and debris particles from a cavity, such as from the mouth, during a dental procedure, and for retraction and protection of the tissue during a dental procedure. This invention relates to the use of a foam pad that is mounted on the end of a tubular dental member, such as a high volume suction tip, which is in turn connected to a vacuum pump.

2. Description of the Prior Art

A common practice is to use a vacuum tip or tubular member or saliva ejector to draw fluids and debris particles from the mouth of a patient during a dental procedure. These vacuum tips or tubular members are attached to a hose, which is in turn attached to a vacuum source, such as vacuum pump. The vacuum tip or tubular member can be either stainless steel or plastic. The plastic tips can be disposable, or they can be cleaned and reused. The distal ends of the vacuum tips can be sufficiently shaped to cut or scrape the inside of a patient's mouth if excessive force is inadvertently applied. The ends of the tubes can be covered by soft tissues in the patient's mouth, and the vacuum can draw the soft tissue into the distal end to close off or seal the tube, preventing evacuation of fluids or debris from the mouth.

Pads covering the tubes to protect against injury have been suggested. U.S. Pat. No. 5,151,094 discloses a suction swab in which a soft foam is mounted on the end of a stem to protect soft structures from injury. Apertures or holes are cut or drilled though the foam to permit fluids to enter the stem. U.S. Pat. No. 5,094,616 discloses a resilient foam sleeve that can be mounted on a tube. The sleeve is open on the end. It has been suggested that sleeves of this type have not performed well because they tend to slip and become dislodged from the end of the tube. U.S. Pat. No. 6,068,477 discloses a foam cushioned aspirator in which most of the inner tubular member is covered by a foam cushion, which has holes near the end, allowing passage of fluids through the foam member and into the tubular member.

SUMMARY OF THE INVENTION

The instant invention does not employ a sleeve, but instead comprises an initially flat foam member that can be folded over the end of an elongate tubular member and secured thereto forming a foam protective pad. The foam protective pad is fabricated from a porous open cell foam, so that fluids and debris particles can pass, without the necessity of forming holes or apertures through the foam pad. This pad increases the debris trapping surface by a factor of at least five times the cross sectional area of a standard high volume tip orifice which functions as a vortex trapping area.

An oral protective pad is removably mountable on an end of an oral vacuum tube. This oral protective pad comprises an initially flat member formed of a material that is sufficiently flexible so that the pad can be partially folded between top and bottom edges to mount the oral protective pad on the oral vacuum tube so that the protective pad partially closes an open end of the oral vacuum tube. The oral protective pad is formed of a porous material so that fluids will be drawn through the oral protective pad and into the oral vacuum tube. The oral protective pad has a first opening through which the oral vacuum tube is insertable and a second opening, separated from the first opening by a portion of the initially flat member forming a retention band. The second opening is defined in part by an upper edge, which extends across the oral vacuum tube opening when the oral protective pad is mounted on the oral vacuum tube.

According to another aspect of this invention the suction apparatus is connectable to a vacuum for removing fluids and debris from an oral cavity during dental procedure. The apparatus includes a tubular vacuum member having an inclined distal end. A protective pad is mounted on the inclined distal end of the tubular vacuum member. The protective pad is fabricated from a porous, flexible material. The protective pad is initially flat and can be folded to mount the protective pad on the tubular vacuum member. The protective pad has first and second openings with the tubular vacuum member extending though the first opening, and with the tubular vacuum member being partially inserted in the second opening. The protective pad is wider than the tubular vacuum member so that the protective pad, when folded, extends completely around the tubular vacuum member.

This suction apparatus when used in a cavity, such as a dental cavity, comprises a tubular vacuum member with a foam pad mounted on a distal end of the tubular foam member in a folded configuration. The surface area of the foam member is greater than the cross-sectional area of the tubular vacuum member so that fluids and particles can be captured from a wider area. The extra width on the pad adds to the catching surface that captures fine dust, such as tooth or filling powder, that can otherwise collect in the back of the patient's throat.

BRIEF DESCRIPTION OF THE DRAWINGS

FIGS. 1A and 1B are views of a prior art vacuum or aspirator tube used for suctioning fluids and debris during a dental procedure.

FIGS. 2A-2D are views of a suction apparatus comprising a tubular member as shown in FIGS. 1A and 1B with a protective foam pad attached to the distal end of the tubular member. FIG. 2A is front view. FIG. 2B is a side view showing how the foam member is partially folded when mounted on the distal end of the tubular member. FIG. 2C is a rear view. FIG. 2D is a view similar to FIG. 2A, but showing an alternate embodiment in which the pad is positioned at a different position to allow more flow through the tubular member.

FIGS. 3A-3D are views of four different embodiments of the foam pad FIG. 3A shows a foam pad with one circular slot and one linear slot. FIG. 3B shows a version in which a linear slot replaces the circular slot of FIG. 3A. FIG. 3C shows an embodiment having three slots, so that the foam pad can be positioned in a relatively lower flow configuration or a relatively higher flow configuration. FIG. 3D is a view similar to FIG. 3C in which the top slot is curved to define a tongue that will stabilize the foam pad on the tubular member.

FIG. 4 is a three dimensional view showing the relative thickness of the foam pad shown in FIG. 3D.

FIG. 5A shows a pad, of the type shown in FIG. 3A, mounted on the tubular member. FIG. 5B shows a pad of the type shown in FIG. 3B mounted on the tubular member. FIG. 5C shows a pad of the type show in FIG. 3D with the tubular member inserted through the lower slot to expose a side or port opening on the tubular member.

DETAILED DESCRIPTION OF THE PREFERRED EMBODIMENTS

Figure 5A:
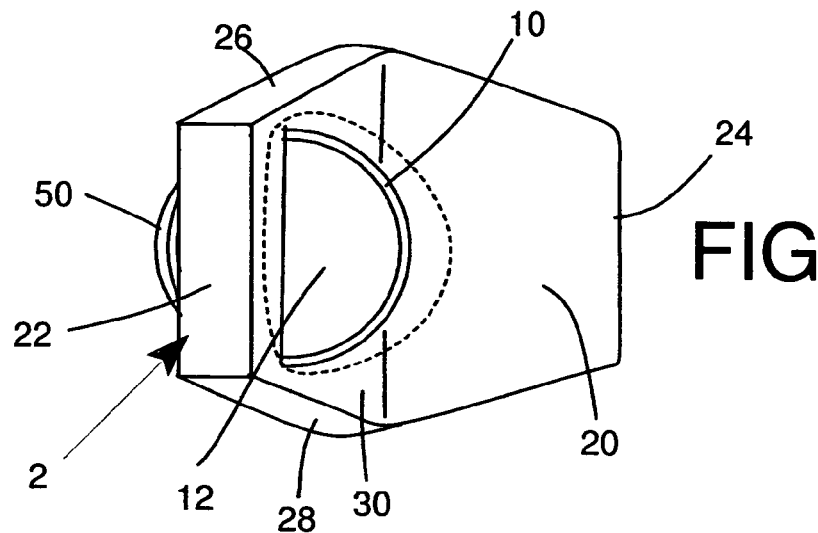
FIGS. 5A-5C are three top views showing pads mounted on the distal end of the tubular member. In each case the pad partially covers the bore of the tubular member.

The instant invention forms a suction apparatus 2 that can be used with a suction system to remove fluids and debris during a dental procedure. This invention employs a conventional oral vacuum tube or tubular vacuum member or aspirator tube 10 of conventional construction, as shown in FIGS. 1A and 1B. Tubular member 10 is open at both ends. An oral protective pad 20 is mounted on a distal end 12 of a tubular vacuum member 10, which is in turn attached to a hose (not shown) at the proximal end 14, so that a vacuum can be applied in the patient's oral cavity when attached to a standard vacuum pump (not shown).

In the preferred embodiment of this invention a relatively thin wall, but rigid, plastic tubular member 10, having at least an S-shaped edge 16 on the distal end 12, is employed. A tubular member or dental aspirator tube of this type can have a diameter of 11 mm and a length of 140-145 mm. Conventional aspirator tubes of this type can a traditional forty five degree cut at one end and one S-shaped cut for increased patient comfort at the opposite end. The different cuttings allow the dentist to choose between them so that he can have two aspirators instead of one. Aspirator tubes of this general type can also have S-shaped openings at both ends, or a forty five degree cut at both ends. A rectangular ventilation hole can be located adjacent to the S-shaped openings Other plastic tubular members can have a straight angled edge, and the protective pad 20 can also be used with those configurations. Both the S-shaped edge and the straight angled edge would from an inclined distal end 12 on the tubular vacuum member 10. A side facing opening or port 18 is also present, adjacent the distal end 12, on the tubular member shown in FIGS. 1A and 1B. This port 18 provides additional flow for a high volume tip. It should be understood, however, that all of the various embodiments of the protective pad 20 can be employed with tubular members that do not have a port 18 in addition to the open distal end 12.

The protective pad 20 is fabricated from a porous, flexible member. An open cell foam, such as a polyurethane foam, can be employed. Reticulated foams can also be employed. Foams of this type are porous and allow relatively unobstructed passages of air, fluids or small debris particles to pass though the foam. As will be subsequently described in more detail, the protective pad 20 will be positioned in the flow path through the distal end 12 of tubular member 10, but the porosity of the foam pad 20 will not unduly interfere with the collection or passage of fluids or debris that need to be drained from the mouth or oral cavity during a dental procedure.

The protective pad 20 is initially a flat member, such as shown in the embodiments of FIGS. 3A-3D as well as in FIG. 4. Individual protective pads 20 can be easily fabricated by cutting or stamping the individual shapes from commonly available flat sheets of open cell or other porous foam. In the preferred embodiment, the individual pads 20 will have a thickness of approximately one-fourth (¼) inch, and therefore can be stamped from a standard flat sheet of quarter inch open cell foam. Other thickness can also be employed. Although the dimensions of the protective pads 20 can differ, the preferred embodiment employs pads having a height of approximately two inches and a width, at the widest central section 30, of approximately one inch. A foam protective pad of this size can be mounted on a tubular vacuum member 10 having an outer diameter of approximately one half (½) inch.

Each of the embodiments of FIGS. 3A-3D has essentially a diamond shape with truncated top and bottom corners. Although this shape is suitable for use with tubular vacuum members 10, it is not critical and other shapes can be employed. Each of the four embodiments shown in FIGS. 3A-3D has a flat top edge 22 and a flat bottom edge 24 having a width that is less than the wider central section 30. Side edges 26 and 28 extend outwardly from the top and bottom edges 22, 24 toward the central section 30. The versions shown in FIGS. 3A-3B have angled corners, but it should be understood, that the pads 10 can be formed with rounded corners. An oval or elliptical shape can also be employed since it is relatively simple to die cut a thin flexible foam of this type in many different shapes.

Each of the versions shown in FIGS. 3A and 313 have at least a first opening 32 and a second opening 34 cut or stamped through the center of the pad 20. Although not absolutely essential, these openings 32 and 34 are on opposite sides of the widest part of the central section 30. Positioning these openings in opposite halves of the pad 10 will make it easy to assembly the pads 10 to the tubular vacuum members 20. It is the shape and number of these openings that distinguish the versions in FIGS. 3A-3D.

FIG. 3A shows an embodiment having a circular first opening 32 and a second opening 34 in the form of a linear slot. The circular first opening 32 would be formed by cutting an removing material from the initially flat member forming the foam pad 20. The linear slot forming second opening 34 can merely be formed by cutting the foam material, without significant removal of material. The tubular member 10 will first be inserted through the first opening 32 and then partially through the second opening 34, but since the foam is flexible, the individual openings will expand to receive at least the distal end 12 of the tubular vacuum member 10. The only difference between the embodiment of FIG. 3B and that of FIG. 3A is that the first opening 32 is also formed as a linear slot. The maximum outer diameter of tubular member 10 can be inserted completely through the linear slot first opening of FIG. 3B.

The first difference between the embodiments of FIGS. 3C and 3D and those of FIGS. 3A and 3B is the inclusion of a third opening 36 between the first opening 32 and the bottom edge 24. The third opening 36 is otherwise identical to the first opening 32 because both the first and third openings 32 and 36 will allow complete insertion of the tubular vacuum member 10 there through so that the distal end 12 can be partially inserted into the second opening 34 when the protective pad 20 is mounted on the tubular vacuum member 10. However, when the tubular vacuum member 10 is inserted through the first opening 32, which is closer to the second opening 34, the foam pad 20 will partially obstruct the port 18 as shown in FIGS. 2A and 2B. When the tubular vacuum member 10 is inserted through the third opening 36, the port 18 will be unobstructed, as shown in FIG. 2D. Although the foam member 20 is porous, a relatively higher volume of fluid will pass through a completely unobstructed port 18 than through a port 18 that is at least partially covered by portions of the foam pad 20.

FIG. 3D differs from the embodiments of FIGS. 3A-3C because the second opening 34 is in the form of a curved slot. This curved slot can be die cut in the same manner as the linear slots, but a tongue 40 is formed by the curved slot opening 34. This tongue 40 will fit into the distal end 12 of the tubular member 10 and will tend to prevent the upper portion of the foam pad 20 from folding over the top of the distal end 12 and possibly becoming dislodged.

A retention band 50 is formed between the first opening 32 and the second opening 34 in each of the embodiments of FIGS. 3A-3D. When the tubular vacuum member 10 is inserted through the third opening 36 in FIGS. 3C and 3D, the foam between the first opening 32 and the third opening 36 will also act as a retention band. After inserting the tubular vacuum member 10, through either the first opening 34 or the third opening 36, the top of the pad 10 is folded back over the distal end 12, which is then partially inserted into the second opening 34. The retention band 50 will then be on the opposite side of the tubular vacuum member 10, and will hold the protective pad 20 on the tubular vacuum member 10, as shown in FIG. 2C.

The pads 20 are designed to increase or decrease the vacuum flow either by trimming the flap or tongue 40 over the open orifice on the distal end 12 to achieve a governing effect suited to the particular patient. This governing effect can also be attained by simply sliding the pad 20 up or down on the vacuum tube 10. Thus the pad 20 can be adjusted on the tube 10 based on the anticipated need for a particular patient or procedure, and the position of the pad 20, and therefore the amount of suction can be altered during the procedure to prevent discomfort and to most effectively remove debris and fluids from the patient's mouth.

Figure 5B:
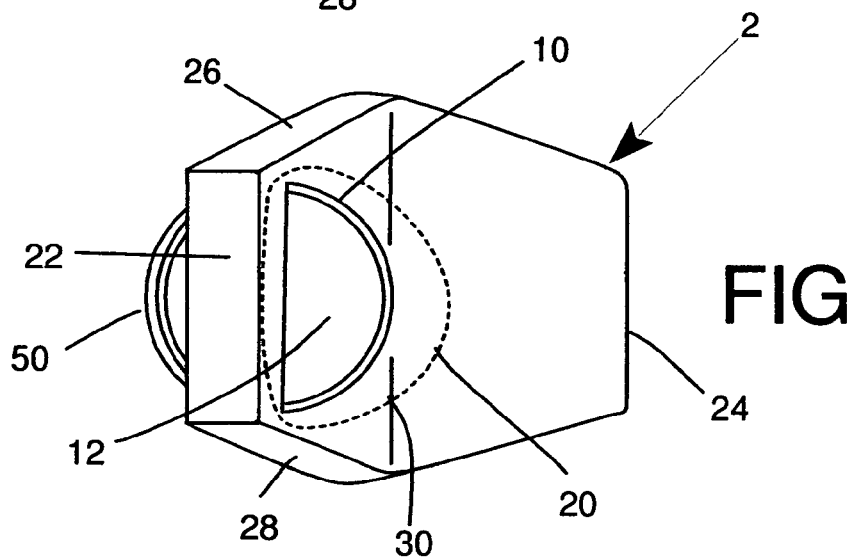
Figure 5C:
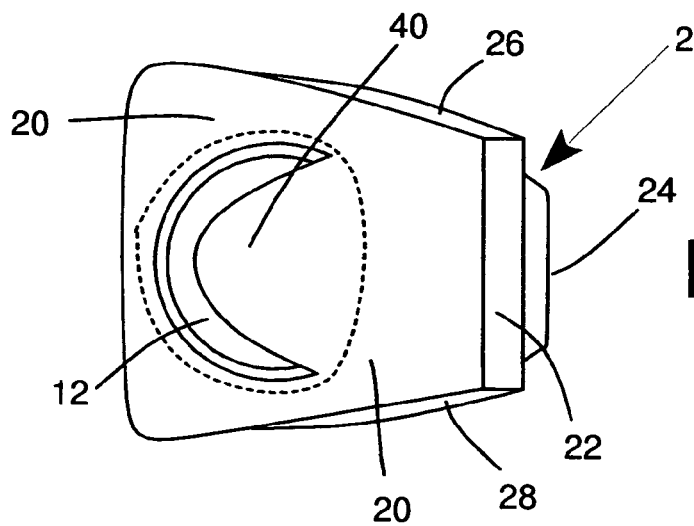

FIGS. 5A-5C are views of the top of the suction apparatus with the pad 20 assembled to the tubular vacuum member 10. Depending upon the relative positions of the openings 32, 34 and 36, the pad 20 will be in position in which it is folded to one degree or another about the central section 30. The relative position of the top edge of pad 22 relative to the distal end 12 can differ, depending on the particular opening configuration FIG. 5A shows the position of the pad 20 shown in FIG. 3A. FIG. 5B shows the position of the pad 20 shown in FIG. 3B. FIG. 5C, shows the pad of FIG. 3D, with the tongue 40 extending into the distal end 12 of tubular member 10. Either of these positions will provide suction, because even though the protective pad 10, partially obstructs the tubular vacuum member 10, the pad 10 is formed from a foam that is relative porous, and the volume of flow into the tubular vacuum member 10, even if it is also through the foam pad 10, will be sufficient to remove fluids and debris from the patient's oral cavity during a dental procedure.

The design of pad 20 allows the patient to evacuate his or her mount by expectorating in front of the lips without stopping or closing the orifice at the distal end 12 of the high volume vacuum tube. When suction is applied to a standard high volume tube, the orifice can be stopped or plugged in the patient's lips are drawn into the end orifice, thereby stopping the vacuum and rendering the standard tube 10 incapable of suctioning off fluids and debris. The use of the tip pad 20 on and tube 10 provides a dual use tip for high volume evacuation from the oral cavity to a spit source outside the mouth. The dual use tip of this invention can replace two separate suction tips that a dental assistant must otherwise handle.

As seen in FIGS. 5A-5C, as well as in the other Figures, the pad 20 extends well beyond the primary orifice at the distal end 12 in which suction is applied. Sufficient area remains in the orifice at the distal end 12 to permit large debris pieces to enter, without obstruction. Since the pad 20 comprises a porous foam, a vacuum is exerted through the foam and fine powder debris can be collected in the foam surrounding the distal end orifice. Thus a larger suction surface is provided that would be available with a prior art high volume tip. By drawing the fine powder into the foam and trapping it there, the fine powder will not accumulate on the soft palate and the sides of the phanangeal area. Gagging is thus reduced eliminating the urge to swallow and reducing coughing, bad taste and the need to expel chips from the patient's oral cavity. The portion of the pads 20 extending beyond the dashed lines in FIGS. 5A-5C is generally the area in which this fine powder will normally be collected.

Figure 6A:
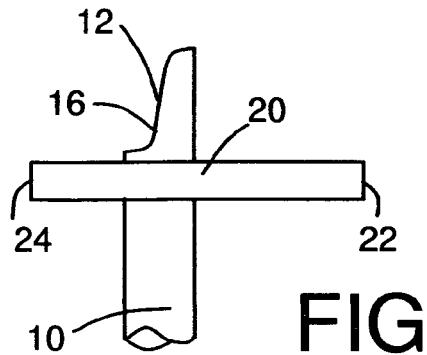
FIGS. 6A-6B show the steps of mounting the protective pad on the tubular vacuum member in the position corresponding to FIG. 2B.
Figure 7A:
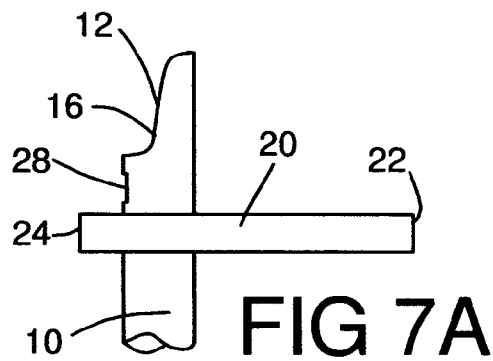
FIGS. 7A-7B show the steps of mounting the protective pad on the tubular vacuum member in the position corresponding to FIG. 2D.
Figure 6B:
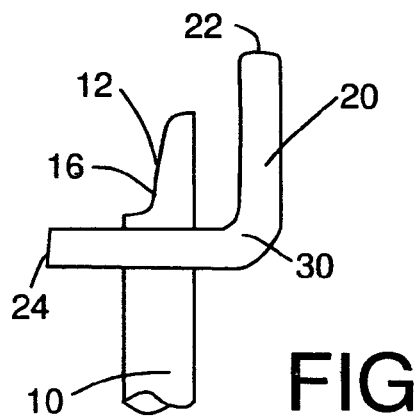
Figure 7B:
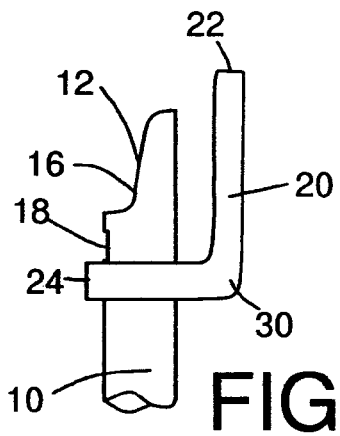
Figure 6C:
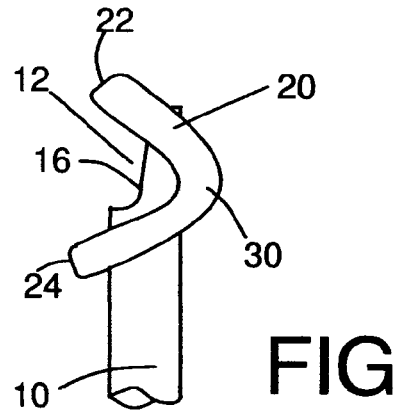
Figure 7C:
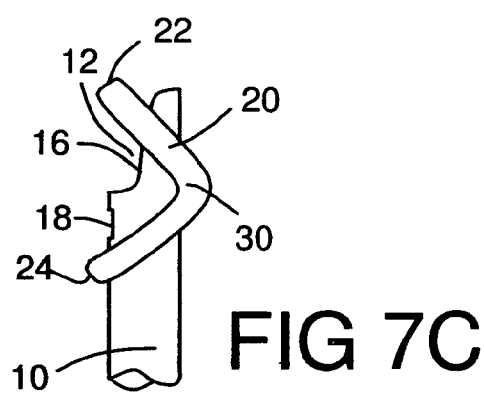

FIGS. 6A-6C show the steps for mounting a protective pad 20 onto a tubular member 10 by inserting the distal end 12 through the first opening 32. FIGS. 6A-6B would thus be applicable to each of the configurations in FIGS. 3A-3D. As shown in FIG. 6A, the tubular member 10 is first inserted through the protective pad 10. The top end 22 of the pad 20 is then folded up about central section 30 as shown in FIG. 6B. Further folding of the top end 22 results in partial insertion of the inclined edge 16 of distal end 12 into the second opening, as shown in FIG. 6C. The foam pad 20 is now held in place in an operative position, so that the device can be used in the patient's mouth. Note that in FIGS. 6A-6B, the pad 20 would extend over the portion of the tubular vacuum member 10 thought which the port 18 would extend. FIGS. 7A-7C, as similar to FIGS. 6A-6B, but the tubular vacuum member 10 is inserted through the third opening 36, which is closer to the bottom pad edge 24 in FIGS. 7A-7C. The steps are the same, but the port 18 remains fully exposed in the operative position of FIG. 7C, which is the relatively higher volume version.

By assembling the pads in this manner, the pads can be economically fabricated from a standard flat foam sheet. The pads can also be easily mounted and easily removed. Individual pads can then be used for only one patient, and then can be immediately disposed of, even if used with a reusable tubular vacuum member.

The foam pad 20 is softer than the end of the plastic tube 10, and will therefore protect delicate areas of the patient's mouth when the suction apparatus 2 is in use. This will prevent pain and potential damage to the patient's tongue, gums and soft tissues of the mouth. The foam pad 20 will also prevent the soft portions of the patient's mouth form being sucked into the distal end 12 of the tubular vacuum member 10, where the distal end 12 might be sealed or the flow restricted. The foam pad 20 will provide a surface area, larger than the cross sectional area of the tubular vacuum member 10, on the opposite sides and along the opposite faces for the vacuum to draw fluids and small debris particles though the open passages in the porous foam. Thus even though the pad might be pressed against the patient's mouth, large areas of the foam pad 20 will remain free for the vacuum to draw fluids and debris through the pad 20 and into the tubular vacuum member 10.

Although the preferred embodiment of this invention is intended for use in dental procedures, it should be understood that a foam protective pad can be combined with a suction tube for use in other applications, such as during medical procedures. The preferred embodiments depicted herein are also merely representative of the numerous embodiments that would incorporate the elements of this invention. Therefore, it is the claims that define the scope of this invention.

I claim:

1. A suction apparatus connectable to a source of a vacuum for removing fluids and debris from an oral cavity during dental procedure; the apparatus comprising:

a tubular vacuum member having an inclined distal end portion;

a protective pad mounted on the tubular vacuum member in a folded configuration, the protective pad being fabricated from a porous, flexible material, the protective pad being formed of an initially flat member and being foldable to mount the protective pad on the tubular vacuum member with flat upper and lower sections of the initially flat member extending at an angle relative to each other;

the protective pad having first and second openings, each extending through the protective pad with the inclined distal end portion extending though the first opening, and with the inclined distal end portion being partially inserted through the second opening;

wherein the protective pad is wider than the tubular vacuum member so that the protective pad, when folded, extends completely around the tubular vacuum member.

2. The suction apparatus of claim 1 wherein the protective pad is more pliant and softer than the tubular vacuum member.

3. The suction apparatus of claim 2 wherein the protective pad comprises a porous foam member.

4. The suction apparatus of claim 1 wherein a portion of the protective pad between the first and second openings extends partially around the tubular vacuum member to form a retention band.

5. The suction apparatus of claim 1 wherein the inclined distal end of the tubular vacuum member has a S-shaped profile.

6. The suction apparatus of claim 1 wherein the second opening comprises a curved opening formed by a curved tongue inserted into the tubular vacuum member to reduce deflection of the protective pad when in use within an oral cavity.

7. The suction apparatus of claim 1 wherein the protective pad is slidable along the tubular vacuum member to adjust the degree to which the pad covers the distal end and to adjust the strength of the vacuum.

8. The suction apparatus of claim 7 further comprising a third opening with the tubular vacuum member being insertable through either the first or the third opening, and the tubular vacuum member further comprises a port adjacent to the distal end, the protective pad covering the port when the tubular vacuum member is inserted through the first opening to form a relatively lower volume suction apparatus and with the port member being exposed when the tubular vacuum member is inserted through the third opening to form a relatively higher vacuum suction apparatus.

\* \* \* \* \*